United States Patent [19]

Frischer et al.

[11] Patent Number: 5,273,902
[45] Date of Patent: Dec. 28, 1993

[54] GENETICALLY MODIFIED VIBRIO

[75] Inventors: Marc E. Frischer; John H. Paul, both of St. Pete, Fla.

[73] Assignee: University of South Florida, Tampa, Fla.

[21] Appl. No.: 785,557

[22] Filed: Oct. 31, 1991

[51] Int. Cl.$^5$ .......................... C12N 1/20; C12N 1/21
[52] U.S. Cl. ............................ 435/252.1; 435/252.3
[58] Field of Search ............... 435/252.1, 252.3, 172.3, 435/409

[56] References Cited

PUBLICATIONS

Frischer et al., Appl. and Environ. Microbiol., 56, (11):3439–3444 (1990).
Stewart et al., Appl. and Environ. Microbiol., 56(6): 1818–1824 (1990).
Fukaya et al., Agric. Biol. Chem., 49(7) 2091–2097 (1985).
Molholt et al., 82(2):477–483 (1978), Biochem. and Biophys. Res. Comm.
Jeffrey et al., Microbiol. Ecol. 19:259–279 (1990).
Lederburg, J. et al., 1946, Gene Recombination in *E. coli*, Nature (London) 260:40–42.
Zinder, N. D. et al., 1952, Genetic Exchange in *Salmonella*, J. Bacteriol. 64:679–699.
Avery, T., et al., 1944, Studies on the Chemical Nature of the Substance Inducing Transformation in Pneumoccocal types. J. Exp. Med. 79:137–159 Stewart, C. J., 1989, The Mechanism of Natural Transformation, pp. 139–164, in S. B. Levy and R. V. Miller (ed.) Gene Transfer in the Environment, McGraw-Hill Book Co., New York.
Stewart, C. J. et al., 1986, The Biology of Natural Transformation, Annu. Rev. Microbiol. 40:211–235.
Coughter, J. P. et al., 1989, Genetic Exchange in the Environment, Antonie van Leeuwenhoek J. Microbiol. 55:15–22.
Jeffrey, W. H. et al., 1990, Natural Transformation of Marine Vibrio Species by Plasmid DNA, Microbiol. Ecol. 19:259–268.
Stewart, G. J. et al., 1990, Detection of Horizontal Gene Transfer by Natural Transformation in Native and Introduced Species of Bacteria in Marine and Synthetic Sediments, Appl. Environ. Microbiol. 56:1818–1824.
DeFlaun, M. F. et al., 1987, Distribution and Molecular Weight of Dissolved DNA in Subtropical Estuarine and Oceanic Environments, Mar. Ecol. Prog. Ser. 38:65–73.
American Public Health Assoc. Standard Method for Examination of Water and Wastewater, 16th Ed. Amer. Pub. Health Assoc., Inc. Washington, D.C. (1985).
Mancini, P. et al., 1987, App. Environ. Microbiol. 53, 665–671.
Oliver, J. D., 1981, Mar. Technol. Soc. J. 15, 45–52.
Brayton, P. R. et al., 1987, Appl. Environ. Microial 53, 2862–2865.
Baumann, P. et al., 1984, Family II, *Vibrionaccae* Veron 1965, 5245 pp. 516–537, in N. R. Kreip and J. G. Hoit (ed.), Bergey's Manual of Systematic Bacteriology, vol. 1, The Williams & Wilkins Co., Baltimore, MD.
Bagdasarian, M. et al., 1981, Specific Purpose Plasmid Cloning Vectors, II. Broad Host Range, High Copy Number, RSF1010 Derived Vectors, and a *Pseudomonas*, Gene 16:237–247.

(List continued on next page.)

*Primary Examiner*—Richard A. Schwartz
*Assistant Examiner*—Nancy T. Vogel
*Attorney, Agent, or Firm*—Reising, Ethington, Barnard, Perry & Milton

[57] ABSTRACT

A high frequency of transformation strain of estuarine Vibrio species is derived from a parent strain naturally transformable with broad-host-range plasmids. The strain has a unique morphology and is generated from the parental strain by transformation by broad-host-range plasmid multimers, a cured of the plasmid by growth of plasmid transformants and nonselective medium resulting in the cured high frequency of transformation strain that transfer significantly more frequently than the parental strain.

5 Claims, 8 Drawing Sheets

OTHER PUBLICATIONS

Carlson, C. A. et al., 1985, Thymidine Salvage in *Pseudomonas Stutzeri* and *Pseudomonas Aeroginosa* provided by Heterologous Expression of *Escherichia coli* thymidine kinase gene. J. Bacteriol. 163:291–295.

Jeffrey, W. H. et al., 1990, Thymidine Uptake, Thymidine Incorporation and Thymidine Kinase Activity in Marine Bacterium Isolates, Appl. Environ. Microbiol. 56:1367–1372.

Meyer, R. et al., 1982, Broad-Host-Range Inc. P-4 Plasmid R1162; Effects of Deletions and Insertions on Plasmid Maintenance and Host Range, J. Bacteriol 152:140–150.

Maniatio, T. et al., 1982, Molecular Cloning, a Laboratory Manual, Cold Spring Harbor Laboratory, Cold Spring Harbor, N.Y.

Griffith, O. M., 1988, Large-Scale Isolation of Plasmid DNA Using High Speed Centrifugation Methods, BioTechniques 6:725–727.

Marmur, J. et al., 1961, A Procedure for the Isolation of Deoxyribonucleic Acid from Microorganisms, J. Mol. Biol. 3:208–218.

Paul, J. H. et al., 1982, Fluorometric Determination of DNA in Aquatic Microorganisms by Use of Hoechst 33258, Appl. Environ. Microbiol. 43:1393–1399.

Buluwela, L. et al., 1989, A Rapid Procedure for Colonly Screening Using Nylon Filters, Nucleic Acids Rec. 17:452.

Church, G. M. et al., 1984, Genomic Sequencing, Proc. Natl. Acad. Sci. U.S.A. 81:1991–1995.

Christopher, F. et al., 1989, Broad-Host-Range Cloning Vectors, pp. 248–267, In C. M. Thomas (ed.) Promiscuous Plasmids of Gram-Negative Bacteria, Acad. Press, Inc. (London), Ltd., London, England.

Borg, D. E., 1989, Transposable Elements in Prokaryotea, pp. 99–137, in S. B. Levy and R. V. Miller (ed.) Gene Transfer in the Environment. McGraw-Hill Book Co., N.Y.

Stewart, G. J. et al., 1990, Detection of Horizontal Gene Transfer by Natural Transformation in Native and Introduced Species of Bacteria in marine and Synthetic Sediments, Appl. Environ. Microbiol. 56:1818–1824.

Rochelle, P. A. et al., 1988, Occurrence, Transfer and Mobilization on Epilithic Strains of Acinetobacier of Mercury-Resistance Plasmids Capable of Transformation, J. Gen. Microbiol. 134:2933–2941.

Frischer, M. E., et al., 1990, Appl. Environ. Microbiol. 56:3439–3444.

Paul, J. H., 1982 Appl. Environ. Microbiol. 43:939–949.

Gawron-Burke, C. et al., 1984, Regneration of Insertionally Inactivated Streptococcal DNA Fragments After Excision of Transposon Tn916 in *Escherichia coli*: Strategy for Targeting and Cloning of Genes from Gram-Positive Bacteria, J. Bacteriol. 159:214–221.

Winstanley, C. et al., 1989 Differential Regulation of Lambda $p_1$ and $P_2$ Promoters by a cI Repressor in a Broad-Host-Range Thermoregulant Plasmid Marker System, Appl. Environ. Microbiol. 55:771–777.

Jeffrey, W. H. et al., 1990, Natural Transformation of a Marine *Vibrio* Species by Plasmid DNA, Microbiol. Ecol. 19:259–268.

GENETICALLY MODIFIED VIBRIO

This invention was made with Government support under National Science Foundation Grant No. OCE 8817172. The Government has certain rights in the invention.

TECHNICAL FIELD

The present invention relates to a high frequency of transformation strain of an estuarine Vibrio species to detect to the propensity of plasmid transformation in aqueous and sedimentary environments.

BACKGROUND OF THE INVENTION

Researchers have identified three mechanisms of gene exchange in bacteria. Conjugation is the cell-contact-dependent plasmid exchange mediated by conjugative plasmids (1). Transduction is gene transfer mediated through bacterio phages (2). Transformation is the process whereby a cell takes up and expresses genes encoded by extracellular DNA (3). Natural transformation is a normal physiological process exhibited by a wide range of bacteria (4, 5). Natural transformation is distinct from artificial transformation, which is a widely used technique in molecular biology for the induction of competence in cells by chemical, enzymatic, or physical means.

There is considerable indirect evidence which suggests that natural transformation may be a mechanism of gene transfer in aquatic environments (6). First, several marine bacterial isolates have been reported to be naturally transformable (7, 8). Second, aquatic environments have been shown to contain an abundance of dissolved DNA which could potentially act as transforming DNA (9).

Microbial gene transfer mechanisms may have evolved as a means for bacteria to adapt to changing environments and may represent a normal function of bacteria in aquatic and terrestrial ecosystems. The use of genetically engineered microorganisms in the environment and the spread of antibiotic resistances resulting from the use of antibiotics in medicine and agriculture may result in what is termed "genetic pollution". Genetic pollution is the introduction of new genetic material or the transfer of genes in the environment resulting from or related to anthropogenic activities. In contrast to other forms of pollution, genetic pollution has the capability of self-propagation once it is established in a component (i.e., recipient) of an ecosystem.

The potential of natural transformation to occur in a aquatic environments has not been studied extensively. However, the issue is significant since the United States Environmental Protection Agency is currently involved in permitting biotechnology firms to use genetically engineered microorganisms in the environment for agricultural, bioremediative, and pest control purposes. To decide whether such genetically engineered microorganisms will be permitted for use, decisions are based upon the nature of the modified gene sequences contained in the cells to be released, the organism to be used and the potential for survival of the organism in the environment. In nearly all instances, the survival of the released organism is determined by some type of viable count, usually a plate count.

Another area of concern regarding gene pools capable of transformation to other cells is the issue of cell killing in waste water facilities. Waste water contains high levels of coliform bacteria and gene transfer by conjugation and transformation has been documented in such environments (10, 11). Chemical disinfection treatments such as chlorination or use of other halogens typically reduce coliform and pathogenic cell counts to acceptably low levels, prior to release of the water into rivers and estuaries. If the genomes (portions of the chromosome or plasmids) survive these treatments either in intact cells or released as free DNA, transfer of genes to the ambient aquatic microbial population can occur. The potential for pathogenic traits and antibiotic resistances to be spread to aquatic bacteria such as Vibrio species, many of which can cause gastroenteritis, septicaemia could result in serious health problems (12, 13).

The present invention provides a high frequency of transformation estuarine strain capable for use in a novel detection system for assaying samples, such as samples containing a potentially useful genetically engineered microorganism or a sample from a waste water facility for the propensity of plasmid transformation in the samples. This provides an indication of the safety of using the genetically engineered microorganism as well as the level of potentially infectious genomes that could survive waste water treatments.

SUMMARY OF THE INVENTION

In accordance with the present invention, there is provided a high frequency of transformation strain of an estuarine Vibrio species, the strain being naturally transformable with broad-host-range plasmids and having unique colony morphology. The strain is generated from a parental Vibrio strain, transformed by broad-host-range plasmid multimers, and cured of the plasmids by growth of plasmid transformants in nonselective medium. The cured high frequency of transformation strain transforms about 6 to 42,850 more frequently than the parental strain.

The present invention further provides a method of detecting the propensity of plasmid transformation in an aqueous or sediment environment. The method generally includes the steps of suspending a culture of the high frequency of transformation (HfT) strain of estuarine Vibrio species as described above in a sample of the aqueous or sedimentary environment and identifying the frequency of transformation of the HfT strain as an indication of the propensity of plasmid transformation in the aqueous environment.

FIGURES IN THE DRAWINGS

Other advantages of the present invention will be readily appreciated as the same becomes better understood by reference to the following detailed description when considered in connection with the accompanying drawings wherein:

FIG. 1 is photomicrograph showing colony morphology of (A) Vibrio strain DI-9, (B) transformant strain WJT-1, and (C) cured strain WI-1C, colonies being grown seven days on artificial seawater agar supplemented with 5 grams of peptone per liter and 1 gram of yeast extract per liter;

FIG. 2 is an autoradiogram of Southern transfer of strain DI-9, transformant strain WJT-1, and HfT strain, WJT-1C probed with [$^{35}$S] labeled Riboprobe RNA probe pJHP-1 Lanes 1, undigested pKT230; 2. XhoI-digested pKT230; 3. undigested DI-9 plasmid DNA preparation; 4. XhoI-digested DI-9 plasmid DNA preparation; 5. undigested WJT-1 plasmid preparation; 6.

XhoI-digested WJT-1 plasmid preparation; 7. undigested WJT-1C plasmid preparation; 8. XhoI-digested WJT-1C plasmid preparation. The faint signals in lanes 3 and 7 are due to contamination from lanes 2 and 6;

FIG. 3 is a photomicrograph of a dot blot of total DNA from parental, transformant, and HfT Vibrio strains. Row A, DI-9 (2,000 [lane 1], 4,000 [lane 2], and 6,000 [lane 3] ng); Row B, pKT230 plasmid (5 [lane 1], 10 [lane 2]; 15 [lane 3], and 50 [lane 4] ng); Row C, MF-1 (2,000 [lane 1], 4,000 [lane 2], and 6,000 [lane 3] ng); Row D, MF-1C (2,000 [lane 1], 4,000 [lane 2], and 6,000 [lane 3] ng). Probed with $^{35}$S-labeled Riboprobe RNA probe pSHPII;

FIG. 4 shows typically binding curves of [$^3$H]lambda DNA by parental strain DI-9(—) and HfT strain WJT-1C(—). (A) Mid-log-phase cells; (B) late-log-phase cells; and FIG. 5 is chart showing natural plasmid transformation in water column microcosms sampled from Tampa Bay (A), oligotrophic surface water from the Gulf of Mexico (B), and surface water from Northwest Providence channel, Bahamas (C). Shown in the top panels of each set of graphs are CFU enumerated on ASWJP, and shown in the bottom panels of each set of graphs are the antibiotic-resistant CFU. The open bars indicate the total bacteria present (WJT-1C recipients only. Experiments for the left panels were all performed in sterile microcosms and experiments for the right panels were performed in the presence of the natural population. No Nutrients indicates that no exogenous nutrients were added, and Plus Nutrients indicates that sterile P and Y were added;

FIG. 6 is a chart showing natural plasmid transformation and sediment microcosms sampled from Tampa Bay (A), the Gulf of Mexico, (B), and the Florida Shelf near Miami (C). Symbols and organization of panels as in legend for FIG. 5 ND, not determined;

FIG. 7 are graphs showing the effect of sediments on water transformants in samples taken near a coral reef in Joulter's Cay, Bahamas. WC, water column transformation assay; WC+Sed. water column containing 3 cm$^3$ of sediments; Sed Only, transformation in sediment o plugs. Total CFU and antibiotic-resistant (ABr) CFU values are per entire microcosm. Symbols and organization of panels are as in legend for FIG. 5; and FIG. 8 is a graph showing the kinetics of transformation of marine Vibrio species with highly purified plasmid multimer DNA (4 μg) in filter assays (), using donors as the source of transforming DNA in filter assays (▲), or with donors as source of transforming DNA in liquid assays in nutrient-free artificial seawater (■).

DETAILED DESCRIPTION OF THE INVENTION

Figure 1:
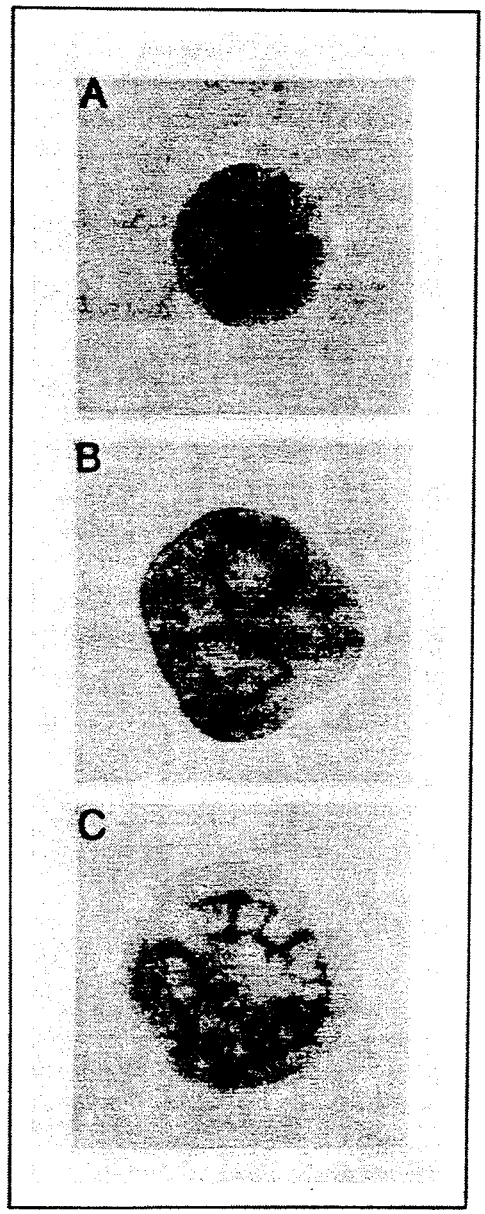

The present invention provides a high frequency of transformation strain of an estuarine Vibrio species (ATCC Nos. 55350, 55351 and 55352), the strain being derived from a parent strain which is naturally transformable with host range plasmids, the strain having unique colony morphology.

The parent estuarine bacterium Vibrio DI-9 has been shown to be naturally transformable with both broad host range plasmid multimers and homologous chromosomal DNA at average frequencies of $3.5 \times 10^{-9}$ and $3.4 \times 10^{-7}$ transformants per recipient, respectively.

The high frequency of transformation strain of the present invention is generated from the parental Vibrio strain, transformed by broad-host-range plasmid multimers, and cured of the plasmids by growth of plasmid transformants in nonselective medium resulting in the cured high frequency of transformation strain that transforms about 6 to 42,850 times more frequently than the parental strain.

The studies detailed below show that the high frequency of transformation HfT variant of the marine Vibrio strain DI-9 can be naturally transformed with plasmid and homologous chromosomal DNA. The data also demonstrates natural plasmid transformation of V. parahaemolyticus, these results suggesting that natural plasmid transformation may be a genus-wide phenotype of Vibrio.

Plasmids used for transformation are Inc P 4 plasmids. The plasmid pAM120 has also been used to successfully transform the HfT Vibrio strain WJT-1C. This plasmid belongs to the Inc P-1 group (31). For example, plasmids used in accordance with the present invention can be selected from the group including pGQ3 and pQSR50.

Applicants have used only natural transformation to get extracellular plasmid DNA into the HfT and parental Vibrio strains as opposed to the many other techniques of artificially inducing transformation including ionic shock, electroporation, and 'biolistics'. However, the transforming material can be diverse. Highly purified plasmid DNA in linear, monomer, and multimer forms have been used. Also plasmid DNA contained in other cells (viable and nonviable) have been used. Any type of plasmid preparation at any level of purity could be potentially used as-transforming DNA in a transformation assay to detect transformation. Many different methods of plasmid purification have been described in the prior art.

Enrichment techniques have also been used to isolate naturally transformable bacteria. The following is an example of such a technique.

1. Determine that bacterium is not either:
    a) resistant to transfer marker(s).
    b) Spontaneous resistance to transfer marker(s) is below detection limit of assay (approx. $10^{-9}$). Streak grown culture of bacterium of interest onto selective media of choice. If growth is not observed proceed.
2. Grow culture of bacterium of interest in desired non-selective media until senescence is reached (usually an overnight culture will suffice).
3. Filter 1 ml of cells onto a sterile 47 mm, 0.2 μm nuclepore filter in a sterile filter apparatus.
4. Transfer filter, cell-side-up, to 47 mm plate containing non-selective media.
5. Overlay cell spot with 4 μg of desired transforming DNA (pasteurized) in a volume of 100 μl. Make-up additional volume with sterile 4.2 mM MgCl$_2$. Usually pQSR50 multimers are used as transforming DNA.
6. Incubate filter overnight at optimum growth temperature. For environmental isolates from S. Florida incubate at 29° C.
7. Next day, aseptically transfer filter to 100 ml of non-selective media in a flask. Incubate at same temperature used previously for one hour. After one hour add antibiotics that are necessary for selection of transforming DNA. In the case of pQSR50 in ASWJP+PY use Km/Str (500/1000 μg/ml). Continue incubation as above overnight.

8. Record whether growth occurred or not. Regardless inoculate 50 mls fresh selective media with one ml. of culture. Continue incubating overnight.
9. If growth occurred streak onto selective plate and incubate. Also, spin down 2×7 mls of culture in two COREX tubes (12,000 rpm for 10 minutes in SS-34 rotor). Mini-prep by standard alkaline lysis procedure.
10. Run mini-preps on gel, if plasmid bands are visible or if not Southern and hybridize with probe to transforming DNA.

If transformation is verified, use this isolate in a standard transformation filter assay to determine the frequency at which transformation occurs.

Since the HfT phenotype is the result of a occurring spontaneous mutation, it should be possible to select for naturally naturally transformable bacteria from the environment by exposing natural populations to general mutagens (e.g. Nitrous Urea, Acidine Orange, UV, Transposon mutagenesis, or any other way to induce random mutations) and then exposing to selectable transforming DNA (e.g. any of the plasmids mentioned earlier. Exogenous isolation: HfT Vibrio strains with selectable markers (e.g. JT-1 which is resistant to Nalidixic acid and Rifampin) are incubated together with a natural community of bacteria in the presence of DNase. After incubation HfT strains which have acquired plasmids which may code for other selectable markers can be selected for on suitable media. In this manner plasmids which are actively participating in transformation could be selected.

Endogenous isolation: Same as above except that instead of incubation with natural microbial community, defined hosts containing plasmids are used as donor strains.

Curing has been accomplished without the aid of mutagens which are known to facilitate the curing process. Curing occurred in the absence of selective pressure (that is, there was no advantage to the maintenance of the plasmid and thus in a portion of the culture over many generations the plasmid was lost. The details of this process are as simple as explained in our paper in Appl. Environ. Microbio. 56:3439-3444 in the section titled 'Curing of plasmids from natural plasmid transformants). This was important since a finding of the research was that the mutation that lead to the HfT phenotype was a naturally occurring one. However, as stated earlier it should be possible to induce a mutation using chemical mutagens which may result in a High Frequency of Transformation phenotype. The results of our work suggest that transformation frequency may be increased by exposing cells to chemical mutagens and screening resulting mutants for transformation ability.

The assay of the present invention generates information transformation frequencies by taking the ratio of total viable bacteria to transformants. In some cases it may not be necessary to generate such frequencies (e.g. it is conceivable that for regulation all that will need to be demonstrated is that transfer occurs below a certain level). In these cases a true transformation frequency would not be required and a most probable number (MPN) method would suffice. Additionally it might be sufficient only to show activity or expression of a product coded by potentially transforming DNA. Thus, assays for activity (if applicable) or expression of mRNA of gene could be utilized. These procedures would not require any cultivation (i.e. plate counts) for detection of transformation.

The present invention further provides a method of detecting the propensity of plasmid transformation in aqueous or sediment environments. In performing the method, a culture of the high frequency of transformation strain of estuarine Vibrio species as described above is suspended in a sample of the aqueous or sedimentary environment to be analyzed. Generally, the frequency of transformation of the HfT strain is identified as an indication of the propensity of the plasmid transformation in the aqueous environment. That is, if there is genome material such as portions of chromosome or plasmids in the sample, the HfT strain will be transformed. Since the HfT strain transforms at such a high frequency, the propensity to transform is highly amplified and detectable.

Transformation frequencies are reported as the number of recipients of transforming DNA to total number of bacteria In the case of the filter assay where only the HfT Vibrio strain is used all colonies appear to have the unique 'wrinkled morphology'. FIG. 1 shows the morphological differences between the parental Vibrio and HfT Vibrio strains and not transformants vs. non-transformants. Transformants are detected by the acquisition of new phenotype encoded by the transforming plasmid DNA and are verified (generally by colony hybridization), by molecular probing. As stated above, methods which do not necessarily involve culture, or enrichment techniques could be used to accomplish the determination of transfer events.

The experimental data below demonstrates the cell-contact dependent transfer of plasmid DNA from bacteria to a marine Vibrio species, this being the first report of intergeneric natural plasmid transformation involving a marine bacterium. This process was concluded to be transformation because it was completely inhibited by DNase I, and neither strain contained conjugative elements or phages. Hence, the present invention can also be used for detecting the propensity of cell contact dependent transfer of plasmid DNA of bacterium in a sample. Alternatively, the test can be used to determine the propensity of microorganisms, most particularly in genetically altered microorganisms, to transfer portions of their genetic contents in situ. Accordingly, the present invention can be used to evaluate the nature of the modified gene sequences contained in genetically engineered microorganisms or naturally occurring microorganisms to be released. Because of the high frequency of transformation of the species of the present invention, the transformation is greatly amplified, as discussed above, to allow identification of the existence of the transformant in the sample. Additionally, the system is amenable to determination of transformation potential of genes in bacterial cells that are chemically or physically inactivated and/or killed, or in extracts from such cells. The following experimental evidence demonstrates the cell-contact dependent transfer of recombinant DNA from both viable and nonviable laboratory genetically engineered bacterial (for example, *E. coli*) to marine bacterial cells (i.e. Hft Vibrio cells). Recently the use of inactivated, dead, or nonviable genetically engineered microbes in the environment has been under consideration for approval by the USEPA. An impediment to the approval process is the inability to determine if the genes from these cells can be transferred by transformation. The invention disclosed herein should enable such a determination to be made.

Protocol for Determination of Transformation Potential of Plasmid DNA encoding Antibiotic Resistances: FILTER ASSAY 1. Media is inoculated with an HfT strain from single colony on plate and incubated overnight at 28° C.
2. The overnight culture is transferred to fresh media and incubated for approximately 16 hours.
3. One ml of culture is filtered onto a sterile filter, and the filter is transferred, cell-sideup, to an agar plate.
4. 4 μg of plasmid multimer or homologous chromosomal DNA is spread on the cell spot and incubated overnight.
5. Cells are serially diluted in sterile ASWJP and plated on non-selective and selective media for determination of antibiotic resistance frequency.
6. The colonies from selective plates are lifted with charged nylon circles and hybridized with [$^{35}$S]probe to determine transformation frequency.

ASSAY IN AQUATIC ENVIRONMENTAL SAMPLES

A. Laboratory Assay
1. A volume of harvested washed, overnight culture of HfT strain is added to a volume of the water sample in a sterile flask (usually 1.0 ml culture per 25 ml sample).
2. 4 μg of Transforming DNA is added and the samples incubated gently with shaking.
3. Cells are harvested by centrifugation or by filtration.
4. Cells are plated on selective and non-selective media.
5. Colonies from selective plates are lifted to charged nylon circles and probed to determine transformation frequency. In situ microcosms.
1. A volume of overnight culture of HfT strain is added to a volume of estuarine water in sterile gas permeable tissue culture bags.
2. Transforming DNA is added and bags are placed in Tampa Bay. The samples are processed as from step 4 of in vitro protocol.

TRANSFORMATION ASSAY IN SEDIMENT SAMPLES

A. Laboratory Assay
1. Surface sediment is added to a sterile 45 cc conical tube. 30 ml of an overnight culture of HfT strain is harvested and resuspended in 300 μl ASWJP and added to 3 cc sediment and mixed.
2. 15 μg Transforming DNA is added, mixed and allowed to incubate.
3. The samples are serially diluted and plated to selected for transformants.
In situ
1. Surface sediment, recipient cells, and transforming DNA are placed in a 25 cc POREX tube.
2. The microcosm is submerged in sediment layer and incubated.
3. Sediment is removed into sterile 45 cc conical tube.
4. The process is continued starting with step 3 of the in vitro protocol.

Protocol to Detect the Transformation Potential of Bacterial 8trains containing Antibiotic-resistance encoding plasmids.

These experiments are conducted in the same manner as described above, except that extracellular transforming DNA is replaced by a donor strain harboring a non-conjugative plasmid. 1. 1.0 ml Bacterial strain containing the plasmid and 1.0 ml recipient [HfT JT-1 (nalidixic acid and rifampicin resistant)] cells are mixed together and filtered onto sterile 0.2 μm Nuclepore filters and the filters placed on ASWJP nutrient agar media or the cell mixture is kept unfiltered in a sterile conical plastic centrifuge tube. For environmental assays, the mixture is added to an aquatic environmental sample (5.0 ml) or 1 cc sediment.
2. The cell mixtures are incubated overnight at 29° C.
3. The transformants are selected on artificial seawater media containing (500 μg/ml kanamycin, 1000 μg/ml streptomycin, and 500 μg/ml Nalidixic acid as for the transformation assays described above. DNase controls are performed simultaneously with these experiments to rule out transduction and conjugation gene transfer events.

Materials and Methods

Bacterial strains. The strains used in this study are listed in Table 1.

TABLE 1

Naturally transforming bacterial strains used in this study

| Strain | Source and characteristics |
| --- | --- |
| Vibrio sp. strain DI-9 | Isolate from Davis Island, Fla. (G. Stewart, University of South Florida, Tampa, Fla.) |
| Vibrio sp. RRVP3 | Spontaneous rifampin-resistant mutant of strain DI-9. Isolated on ASWJP-PY - 500 μg of rifampin per ml (this study) |
| Vibrio sp. MF-1 | DI-9 naturally transformed with pGQ3 |
| Vibrio sp. MF-1C | MF-1 cured of the plasmid pGQ3 |
| Vibrio sp. MF-3C | MF-1 retransformed with pGQ3 and cured |
| Vibrio sp. WJT-1 | DI-9 transformed with pKT230 (16a) |
| Vibrio sp. WJT-1C | WJT-1 cured of the plasmid pKT230 |
| V. parahaemolyticus USFS 3420 | G. Stewart (University of South Florida, Tampa, Fla.) |

Strain DI-9 has been identified as Vibrio species (7). To verify the identity of transformants, HfT strains, and the parental Vibrio strain, biochemical taxonomic tests were performed (14) as well as phenotypic profiling using API 20E test strips (Sherwood Medical, Plainview, N.Y.).

Transforming DNA and gene probes. The plasmids used in transformation studies were the broad-host-range Inc P4 plasmids pGQ3 and pQSR50. Both these plasmids encode for resistance to the antibiotics kanamycin and streptomycin. pGQ3 is a derivative of pKT230 (15) that contains the Escherichia coli thymidine kinase gene (16, 17). pKT230 is a derivative of RSF1010 and pACYC177 (15). pQSR50 is a TN5-containing derivative of the plasmid R1162 (18). Portions of these plasmids were subcloned into the Riboprobe vector pGEM3Z or pGEM4Z. [$^{35}$S]RNA probes were prepared by transcription of the subcloned fragments with T7 or SP6 RNA polymerase. Using [$^{35}$S]UTP (1,320 μCi/mmol; NEN Research Products, Boston, Mass.) as described by Promega (Riboprobe system or Riboprobe Gemini System. Transcription of cloned DNA, Promega Technical Bulletin 002, Promega Biotech, Madison, Wis. 1988). Chromosomal DNA from a spontaneous rifampin-resistant mutant of DI-9 (RRVP3) was used as transforming DNA for the chromosomal transformation assay.

Preparation of transforming DNA. Plasmids were amplified in *E. coli* cultures, using chloramphenicol and uridine as described by Maniatis et al. (19). Large-scale plasmid DNA purification was performed by alkaline lysis as described by Griffith (20). To further separate plasmid from chromosomal DNA, the plasmid extract was passed through a pZ523 column (5'→3' Inc., West Chester, Pa.). Plasmid multimers were prepared as described by Jeffrey et al. (7). The degree of multimer formation was judged by visualization on a 0.4% agarose gel with the fluorochrome Hoechst 33258. Chromosomal DNA wa prepared by the method of Marmur (21). All DNA concentrations were determined by the Hoechst 33258 method (22).

Culture conditions Strain DI-9 and the HfT strains were grown in artificial seawater with 5 grams of peptone per liter and 1 gram of yeast extract (ASWJP+PY[23]) per liter. For transformation assays, cells were grown to an optical density of 0.8 at 600 nm at room temperature ($26°\pm2°$ C.) which corresponds to approximately $2 \times 10°$ cells per ml or late log phase (data not shown).

Filter transformation assay. In transformation assays, i ml of late-log-phase cell culture was immobilized onto a sterile Nuclepore filter (47 mm; 0.2-μm pore size) (Nuclepore Corp., Pleasanton, Calif.), keeping cells to a spot of no more than 1.5-cm diameter. The filter was then transferred aseptically cell-side-up onto an ASWJP+PY agar plate and overlaid with 4 μg of pasteurized plasmid multimers suspended to a final volume of 100 μl in sterile deionized water of 4.2 mM $MgCl_2$. Pasteurization of DNA was accomplished in incubation at 75° C. for two hours. Cells were allowed to incubate 16 hours at room temperature. Following incubation, the filter was transferred to 10 ml of ASWJP+PY and allowed to shake at approximately 200 rpm for one hour. This was necessary to resuspend the cell mat and to allow the cells to recover before exposure to antibiotic selection. Cells were then serially diluted and plated on selective (ASWJP_PY and 500 μg of kanamycin per ml, 1,000 μg of streptomycin per ml) and nonselective media (ASWJP+PY) and enumerated after 48 to 72 hours of growth. Chromosomal filter transformation assays were done identically as plasmid filter transformation assays, except that 10 μg of homologous chromosomal DNA from RRVP3 was placed on the cell spot. Selection for transformants was on ASWJP+PY containing 500 μg of rifampin. All antibiotics used in these studies were purchased from Sigma Chemical Co. (St. Louis, Mo.).

Figure 2:
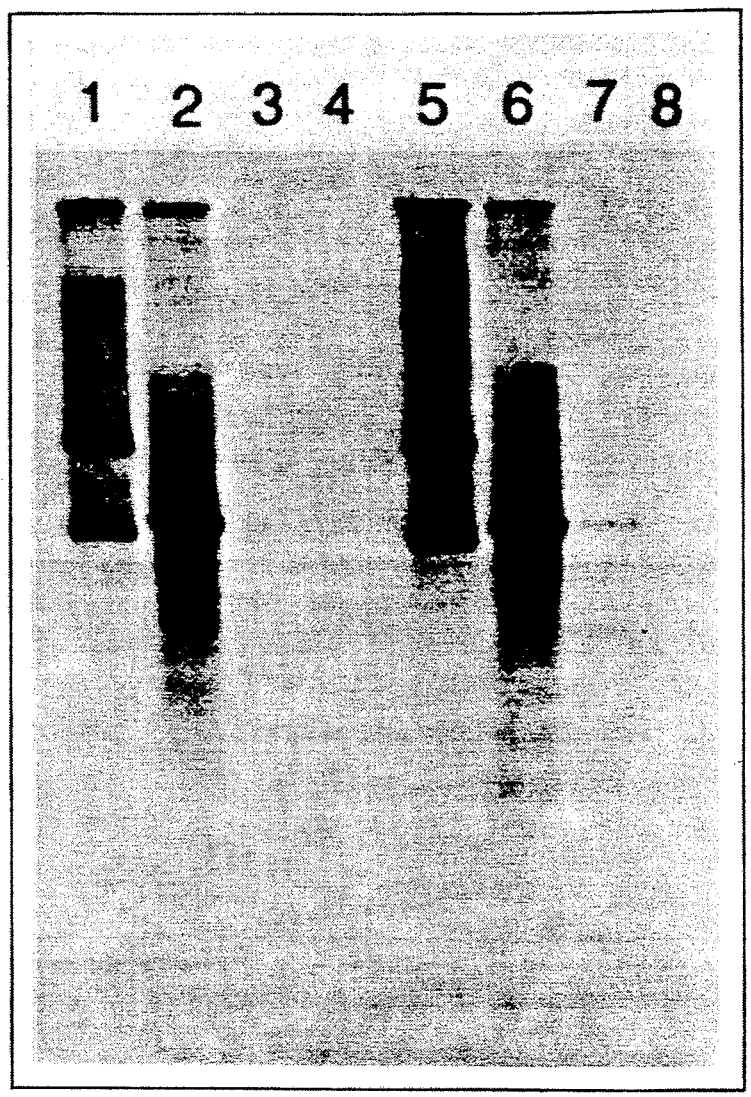

Verification of plasmid transformation. Presumptive plasmid transformants, identified as antibiotic-resistant colonies, were transferred to charged nylon circles and grown on the filter until colonies were visible (24 to 48 hours). Colonies were lysed on the filters by the method of Buluwela et al. (23) and the DNA was denatured and fixed by the method described by Maniatis et al. (19). It was found that the combination of those two procedures yielded a more distinct hybridization signal than either method alone (data not shown). Filters were hybridized overnight with [$^{35}$S]RNA probes at 42° C. essentially by the method of Church and Gilbert (24) and modified as described by Promega Technical Bulletin 002. Filter washing consisted of was in $2 \times SSC$ (0.3M NaCl, 0.03M sodium citrate [pH 7.0] containing 1 mM dithiothreitol) for five minutes at room temperature followed by three 60 minutes washes at 65° C. in PSE (0.25M sodium phosphate, 2% sodium dodecyl sulfate, 1 mM EDTA, pH 7.4) and three 30 minute washes in PES (40 mM sodium phosphate, 1% SDS, 1 mM EDTA, pH 7.4) at 65° C. Filters were dried and hybridization was detected by autoradiography. Colonies were also subcultured and the plasmid DNA was extracted by the miniprep method of Maniatis et al. (19). Transforming plasmid DNA could be identified in the transformants by Southern blotting and probing with gene probes as described above (FIG. 2).

Curing of plasmids from natural plasmid transformants. DI-9 plasmid transformants were cured of their plasmids by growth in ASWJP+PY without antibiotics. After five successive 24-hour transfers to fresh medium, the culture was serially diluted and plated onto nonselective medium. After growth, the colonies were replica plated to selective medium. Colonies which failed to grow in the presence of antibiotics were selected.

DNA binding studies. [$^3$H]DNA was prepared by end labeling HindIII-digested lambda DNA with all four [$^3$H] deoxynucleoside triphosphates. To measure DNA uptake rates of DI-9 and WJT-1C, cultures were diluted to approximately $2 \times 10^8$ cells per ml in freshly autoclaved, sterile filtered ASWJP+PY in an acid-washed polymethylpentene flask. End-labeled [$^3$H]DNA was added to diluted culture (0.25 μC/ml, 3 ng/ml). Triplicate 2-ml samples were filtered onto Nuclepore filters (pore size 0.2 μm) at time intervals ranging from 0 minutes to 4 hours. After the sample had passed through the filter with mild vacuum (10 mm Hg), the filters were immediately washed with 3 ml of sterile filtered ASWJP containing 10 μg of calf thymus DNA per ml to prevent further DNA binding of labeled [$^3$H]DNA. Filters were then placed in scintillation vials containing 0.5 ml of 0.5M Protosol (NEN Research Products, Boston Mass.) to solubilize the filter. After the filters were completely dissolved, 25 μl of glacial acidic acid and 10 ml of Ecoscint O scintillation counting fluid (National Diagnostics, Manville, N.J.) was added to the vial, and the radioactivity associated with the filter was determined by liquid scintillation counting. Nonspecific binding of DNA by medium particulates was assessed in cell-free controls. Nonspecific binding generally contributed less than 10% of overall binding compared with the 30 minute time points with cells present. Background counts were routinely subtracted from all experiments.

RESULTS

Table 2 shows the results of plasmid multimer transformation of Vibrio strain DI-9 and *V. parahaemolyticus*.

TABLE 2

| Natural transformation filter assay of wild-type and HfT marine strains with plasmid multimer DNA | | | | |
|---|---|---|---|---|
| Strain | DNA | Transformation[a] | Transformation frequency | HfT/KI-9 ratio |
| Wild-type strain | | | | |
| Vibrio strain DI-9 | pGQ3 | + | $<1.4 \times 10^{-9b}$ | |
| | pQSR50 | + | $3.5 \times 10^{-9}$ | |

TABLE 2-continued

Natural transformation filter assay of wild-type and HfT marine strains with plasmid multimer DNA

| Strain | DNA | Transformation[a] | Transformation frequency | HfT/KI-9 ratio |
|---|---|---|---|---|
| *V. parahaemolyticus* | | | | |
| USFS 3420 | pGQ3 | — | $<1.0 \times 10^{-9}$ | |
| | pQSR50 | + | $1.9 \times 10^{-9}$ | |
| HfT Vibrio strains | | | | |
| MF-1C | pGQ3 | + | $0.9 \times 10^{-6}$ to $6.6 \times 10^{-6}$ | 6–47 |
| WJT-1C | pGQ3 | + | $2.3 \times 10^{-6}$ to $6.7 \times 10^{-6}$ | 16–48 |
| MF-3C | pGQ3 | + | $1.3 \times 10^{-6}$ | 9 |
| MF-1C | pQSR50 | + | $0.2 \times 10^{-5}$ to $1.1 \times 10^{-5}$ | 571–3.143 |
| WJT-1C | pQSR50 | + | $0.01 \times 10^{-4}$ to $1.5 \times 10^{-4}$ | 286–42.857 |
| MF-3C | pQSR50 | + | $2.5 \times 10^{-6}$ | 714 |

[a]+, Transformation was detected; —, transformation could not be detected
[b]Transformation could be detected only after liquid enrichment (16a).

Transformation of Vibrio strain DI-9 occurred with plasmid multimers of pQSR50 and pGQ3 at frequencies of $3.5 \times 10^{-9}$ and $\leq 1.44 \times 10^{-9}$ transformants per recipient, respectively (Table 2). A strain of *V. parahaemolyticus* (USFS 3420) was also naturally transformed with plasmid DNA at a frequency of $9.7 \times 10^{-10}$ transformants per recipient with pQSR 50 plasmid multimers.

Isolation of HfT strains. Several DI-9(pGQ3) transformants were cured of their plasmids by successive growth in nonselective medium. The transformants and cured strains possessed a colony morphology distinct form that of the original (parental) strain DI-9 (FIG. 1). The biochemical phenotype profile of all the cured strains were identical to that of DI-9 as determined by the API 20E test strip (Sherwood Medical). DI-9 and all the cured strains are rod shaped, motile (a single polar flagellum), oxidase positive, and able to ferment glucose.

The results of natural plasmid transformation assays of the plasmid-cured strains appear in Table 2. When reexposed to plasmid multimers, these cured strains transformed at significantly higher frequencies than the parental strain DI-9. Transformation frequencies of the cured strains MF-1C, WJT-1C, and MF-3C ranged from $9 \times 10^{-9}$ to $6.7 \times 10^{-8}$ transformants per recipient with pGQ3 multimers or were 6 to 48-fold greater than the transformation rate of the parental strain DI-9. The cured strains transformed at frequencies ranging from $1 \times 10^{-6}$ to $1.5 \times 10^{-4}$ transformants per recipient with pQSR50 plasmid multimers or 286 to 42,857 more efficiently than the parental strain DI-9. These strains are referred to as HfT strains. Plasmid transformants could be identified by Southern hybridization (FIG. 2) or directly by colony hybridization with the appropriate labeled gene probe (data not shown).

Figure 3:
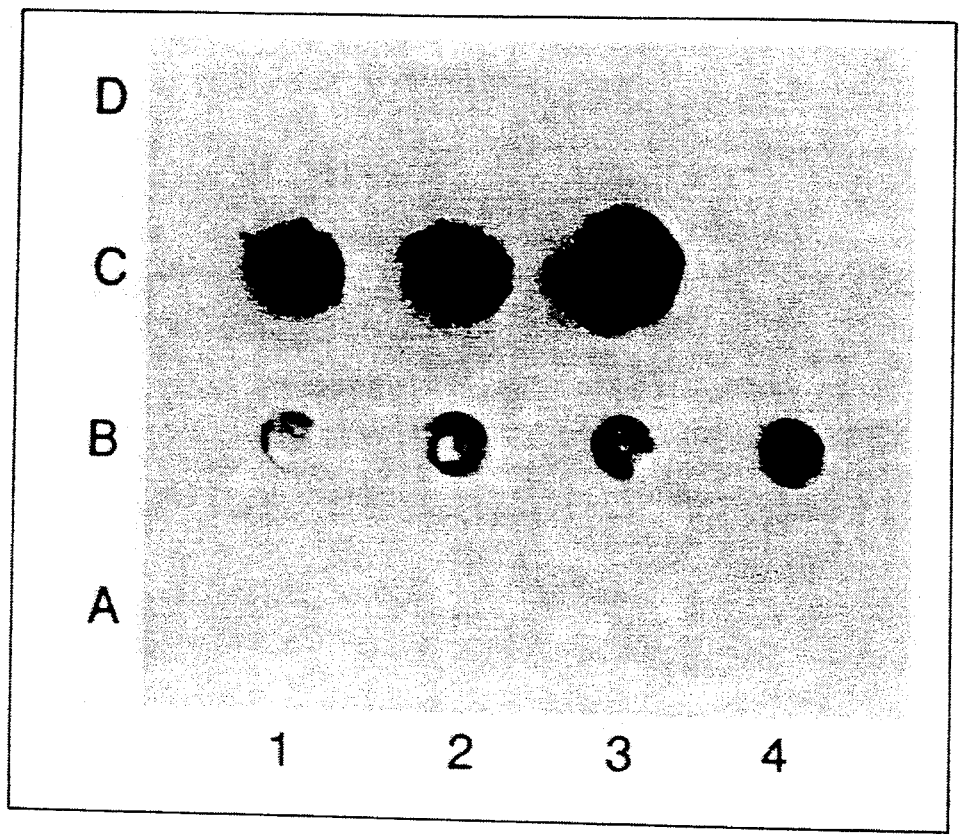

To rule out the possibility that these high transformation frequencies were caused by homology resulting from transforming plasmid DNA remaining in the HfT strains, a dot blot of a total DNA preparation from the HfT strain MF-1C was hybridized with a probe (pJHP II) made to the original transforming DNA (FIG. 3). Concentrations of DNA dotted on the filter were sufficient to detect a single copy of the plasmid inserted into the chromosome. No hybridization was found with the parental strain DI-9 or the cured strain MF-1C, whereas strong hybridization occurred with the DI-9(pGQ3) transformant MF-1 (FIG. 3). These results indicate that no sequences from the transforming DNA remained in the cured strains.

Table 3 shows the result of chromosomal transformation studies with the wild-type and HfT strains.

TABLE 3

Natural filter transformation of wild-type and HfT marine strains with Rif[b] chromosomal DNA from RRVP3

| | Treatment[a] | | | |
|---|---|---|---|---|
| Strain | CT DNA | Rif[b] DNA | Rif[b] DNA + DNase I | Frequency |
| DI-9 | $2.7 \times 10^{-7}$ | $6.1 \times 10^{-7}$ | $2.2 \times 10^{-7}$ | $3.4 \times 10^{-7}$ |
| WJT-1C | $3.3 \times 10^{-7}$ | $8.3 \times 10^{-5}$ | $1.1 \times 10^{-7}$ | $8.3 \times 10^{-5}$ |

[a]CT DNA, Calf thymus chromosomal DNA;
Rif[b] DNA, chromosomal DNA from RRVP3;
Rif[b] DNA + DNase I, chromosomal DNA from RRVP3 and DNase I(100 Kunitz).

WJT-1C was transformed at a frequency of $8.3 \times 10^{-3}$ transformants per recipient (Table 3). This represents a 244-fold increase in chromosomal transformation frequency compared with that of the parent DI-9. This increase in transformation efficiency cannot be explained by the presence of plasmid DNA residing in the HfT strains, since Vibrio strain DI-9 chromosomal DNA has no homology to these plasmids (FIG. 3).

Figure 4A:
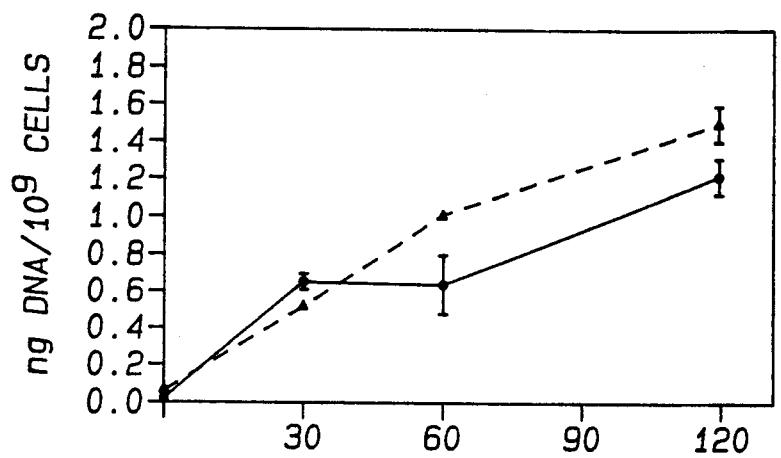
Figure 4B:
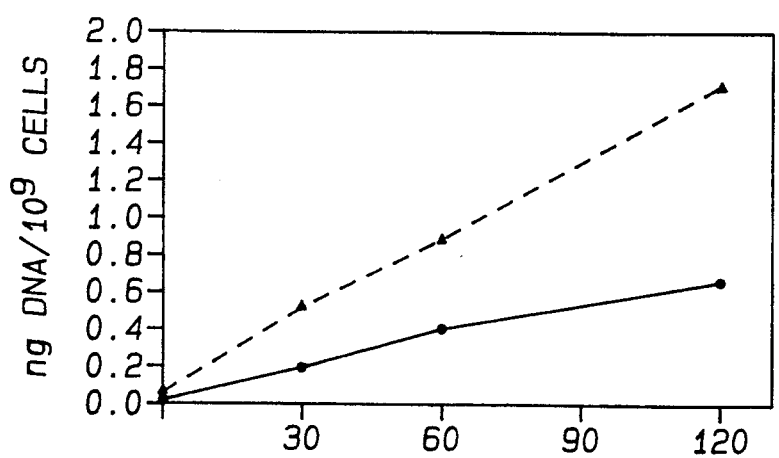

[3H]DNA binding studies FIG. 4 shows the results of a typical [3H]DNA uptake experiment with parent strain DI-9 and HfT strain WJT-1C. Binding rate comparisons within each experiment revealed that mid-log-phase cultures of both strains bound heterologous DNA similarly (FIG. 4A), while late-log-phase cultures of WJT-1C bound heterologous DNA approximately twice as fast as DI-9 during the first 30 minutes of exposure to labeled DNA (FIG. 4B). Uptake rates varied dramatically between experiments, but ratio of the short-term (30 minute) uptake rates of DI-9 and WJT-1C remained fairly constant. Incubation temperature before and during exposure to DNA may greatly effect the DNA uptake rate DI-9 and the HfT strains will grow at temperatures ranging from 15° to 39° C., with optimum growth rates at 37° C. Uptake studies performed at 28° C. yielded 6 to 2,383 times that uptake rate of those performed at room temperature (20° to 23° C). Mid-log-phase cultures of both strains possessed similar DNA uptake rates. The ratio of WJT-1C to DI-9 uptake rate for mid-log-phase cells was $0.918 \pm 0.219$ ($0.1 < P < 0.025$, $n=5$). In contrast, the initial uptake rates of late-log-phase cultures were approximately twofold greater ($2.1 \pm 0.59$) for the Hft strain than for the parental DI-9 ($0.02 < P < 0.05$, $n=4$ [Table 4]).

TABLE 4

Short-term binding rates of [$^3$H]DNA by wild-type (DI-9) and HfT (WJT-1C) marine Vibrio strains

| Experiment no.[a] | DNA binding rate (ng of DNA/$10^9$ cells/min) | | |
|---|---|---|---|
| | DI-9 | WJT-1C | WJT-1C/DI-9 |
| Mid log phase[b] | | | |
| 1 | 0.233 | 0.166 | 0.712 |
| 2 | 0.020 | 0.016 | 0.800 |
| 3 | 0.007 | 0.008 | 1.130 |
| 4 | 1.350 | 1.040 | 0.770 |
| 5 | 1.410 | 1.670 | 1.180 |
| Late log phase[c] | | | |
| 6 | 0.0006 | 0.0016 | 2.67 |
| 7 | 0.0200 | 0.0430 | 2.15 |
| 8 | 0.0040 | 0.0092 | 2.29 |
| 9 | 1.1280 | 1.4300 | 1.28 |

[a]Experiments 1 to 3 and 6 to 8 were performed at room temperature, and experiments 4, 5, and 9 were performed at 28° C.
[b]Average ratio of WJT-1C/DI-9 = 0.918 ± 0.219, t = 0.837 (0.1 < P < 0.25).
[c]Average ratio of WJT-1C/DI-9 = 2.10 ± 0.588, t × 3 735 (0.02 < P < 0.05).

The above data demonstrates the isolation of the HfT variant of the marine Vibrio strain DI-9 which can be naturally transformed of plasmid or homologous chromosomal DNA. The data also demonstrates natural plasmid transformation of a *V. parahaemolyticus* thereby suggesting that natural plasmid transformation can be genus-wide phenotype of Vibrio.

The parental Vibrio strain DI-9 was previously shown to transform with the broad-host-range plasmid pKT230 and pGQ3 at a frequency of $0.3 \times 10^{-8}$ to $3.1 \times 10^{-8}$ transformants per recipient (7). The above data shows the broad-host-range plasmids pGQ3 and pQSR50 used as transforming DNA. The HfT strains transformed at significantly greater frequencies than the wild type with both plasmids and homologous chromosomal DNA. Transformation frequencies of the HfT strains varied by four orders of magnitude, depending upon the transforming DNA employed. Use of pQSR50 plasmid multimers as transforming DNA consistently resulted in the highest transformation frequencies by nearly two orders of magnitude. This was surprising since pGQ3 and pQSR50 are derived from plasmids which are thought to be identical (RSF1010 and R1162, respectively) (25). Because pQSR50 carries the transposon Tn5, it was conceivable that the transposon played a role in the increased transformation efficiency observed for this plasmid. It was speculated that illegitimate recombination events encoded for by transposition genes could have accounted for the higher frequency of transformation with pQSR50. Transposons which mediate their own conjugal transfer have been reported previously (26), although this phenomenon has not been reported for transformation. Thus, illegitimate recombination events may have circumvented the need for homology required with normal recA type-mediated recombination, which is believed to occur in natural transformation (5). However, transformation of WJT-1C occurred with R1162, the Tn5-free precursor of pQSR50, at an even greater frequency (data not shown).

The efficiency of transformation was over two orders of magnitude greater with chromosomal DNA for the HfT variants than the parental DI-9 strain. This indicates that the HfT phenotype was not associated with a condition that involved efficient plasmid transformation (i.e, plasmid uptake or recircularization). These results also demonstrate that the high transformation frequencies observed in the HfT strains were not caused by plasmid DNA either remaining free in the cell or incorporated in the chromosome of the Hft (cured strains) which could have provided DNA homology for plasmid transformation. There was no homology between the transforming chromosomal DNA and any of the plasmids employed.

EXPERIMENTAL EVIDENCE #2

Materials and Methods

Strains and transforming DNA. The HfT Vibrio strain WJT-1C was used as the recipient in the following studies. The broad-host-range plasmid pQSR50 was used as transforming DNA. Plasmid DNA and plasmid multimer preparations were performed. Plasmid multimers have been shown to transform at an approximately 10-fold-greater frequency than plasmid monomers.

Sampling sites. Water samples for water column microcosm studies were collected from Bayboro Harbor, St. Petersburg, Fla., the Gulf of Mexico (24°49.94'N, 85°20.00'W), and the Northwest Providence Channel, Bahamas (26°07.90'N, 78°32.50'W). Sediments were collected from North Shore Beach, St. Petersburg, Fla., the Gulf of Mexico near the mouth of Tampa Bay (28°33.89'N, 82°55.03'W), and near Miami (25°45.10'N, 80°04.94'W). Samples for sediment-water column combination microcosms were taken near a coral reef at Joulter's Cay, Bahamas.

Water column transformation assays. A 25-ml overnight culture of WJT-1C grown in ASWJP PY was harvested by centrifugation and resuspended in 20 ml of sterile seawater medium lacking an organic carbon source (ASWJP). A 1-ml (for estuarine microcosms) or 0.5-ml (for Gulf of Mexico and Bahamas microcosms) amount of the cell suspension was added to 24 or 24.5 ml, respectively, of the seawater sample to be investigated. Seawater was either autoclaved and sterile filtered (ASF) or used directly (within two hours of collection) and added to 50-ml disposable centrifuge tubes. Nutrients were added to 50 ml disposable centrifuge tubes. Nutrients were added to some treatments in the form of sterile-filtered solutions of peptone (P) and yeast extract (Y) for final concentrations of 5 mg of P per ml and 1 mg of Y per ml for the estuarine experiment, 0.2 mg of P per ml and 0.04 mg of Y per ml for the Gulf of Mexico experiment, and for the Bahamas experiment, 0.1 mg of P per ml and 0.02 mg of Y per ml (low nutrients) and 1 mg of P per ml and 0.2 m of Y per ml (high nutrients). Five micrograms of transforming DNA (pQSR50 multimers) was added, and the mixtures were incubated for 10 to 24 hours on a gyratory shaker at 1 to 3 rpm at 25° to 30° C. The cells were harvested by either centrifugation or filtration onto a sterile 47-mm Nucleport filter. The pellets or filters were placed in 5.0 ml of sterile ASWJP, and the cells were resuspended by vortexing for one to two minutes. Aliquots of the suspension were diluted and plated in ASWJP+PY for enumeration of total CFU and in ASWJP+PY containing 500 µg of kanamycin per ml, 1,000 µg of streptomycin per ml, and $5 \times 10^{-6}$M amphotericin B to detect transformants. The unique colony morphology of WJT-1C allowed enumeration of recipients on nonselective plates in the presence of the ambient population. Transformants in sterile-seawater experiments were enumerated directly on antibiotic plates (spontaneous mutation of resistance to kanamycin and streptomycin has never been observed for WJT- 1C). Presumptive transformants from all experiments in the presence of the ambient community were verified by colony hybridization of antibiotic plates (8) using the neomycin-kanamycin phosphotransferase gene (nptII) of pQSR50 as a probe. Filters were hybridized with $^{35}$S-RNA probes as described previously.

Sediment transformation assays. Sediment column transformation assays (8,17) were performed with estuarine and Gulf of Mexico sediments, whereas transformation assays were performed in sediment plugs for Miami samples. These methods were found to yield equivalent results (data not shown). For sediment columns, 3 cm$^3$ of freshly collected sediment or autoclaved sediment was used to load columns. When sterile sediment was employed, it was washed twice with sterile ASWJP and charged with 3 ml of 5-$\mu$g/ml calf thymus DNA for one hour to saturate binding sites that had endogenous nucleic acids destroyed above, harvested, and resuspended in 1/10 the original volume of ASWJP, and the cells were added. The columns were incubated for 16 to 24 hours at 25° to 28° C. The columns were aseptically dismantled, and the sediment was resuspended in 5.0 ml of sterile ASWJP by 2 minutes of vigorous vortexing. The overlaying fluid was immediately plated as described above. For sediment plug transformation assays, 3 cm$^3$ disposable conical centrifuge tube. Recipient cells (30-ml culture resuspended in 100 $\mu$l), transforming DNA (15 $\mu$g), and, in some treatments, nutrients (5 mg of P, 1 mg of Y), were added each in 100-$\mu$l volumes, and the sediment was mixed with a sterile pipette. The plugs were incubated overnight and resuspended in 5.0 ml of sterile ASWJP. This suspension was prepared for plating as in the sediment column assays, and presumptive transformants were verified by colony hybridization as described previously.

Sediment-water column combination transformation assays. To determine the effect of sediments on water column transformation, transformation assays were performed in 25.0 ml of seawater, 25.0 ml of seawater containing 3 cm$^3$ of sediment, and 3-cm$^3$ sediment plugs. Recipient cells were grown as described previously, harvested, and resuspended in 1/10 volume ASWJP, and 0.5 ml of cells was added to each treatment. Five micrograms of transforming DNA was added, and the mixtures were incubated overnight at 25° to 28° C. The cells were harvested by either filtering directly and resuspending the filter in 5.0 ml of ASWJP or adding 5.0 ml of ASWJP to the sediment directly. The sediment and filters were vortexed vigorously for two minutes and the liquid was plated as described above.

Transfer to the indigenous flora. In most of the experiments performed above, at least one sample received the transforming DNA and no WJT-1C recipients, while a replicate sample received no recipients and calf thymus DNA. Samples were plated as described above, and the antibiotic resistant colonies were probed for the presence of the nptII gene. Liquid enrichments were also made of transformation assays and cells were extracted and probed as previously described (17).

RESULTS

Figure 5A:
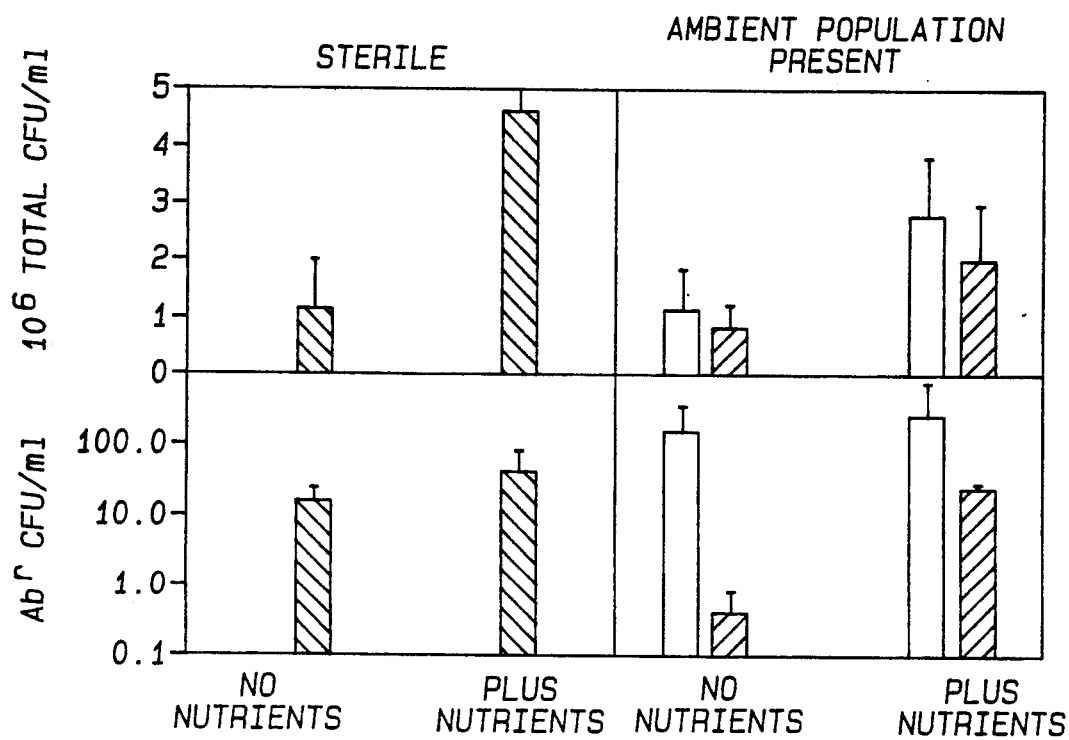
Figure 5B:
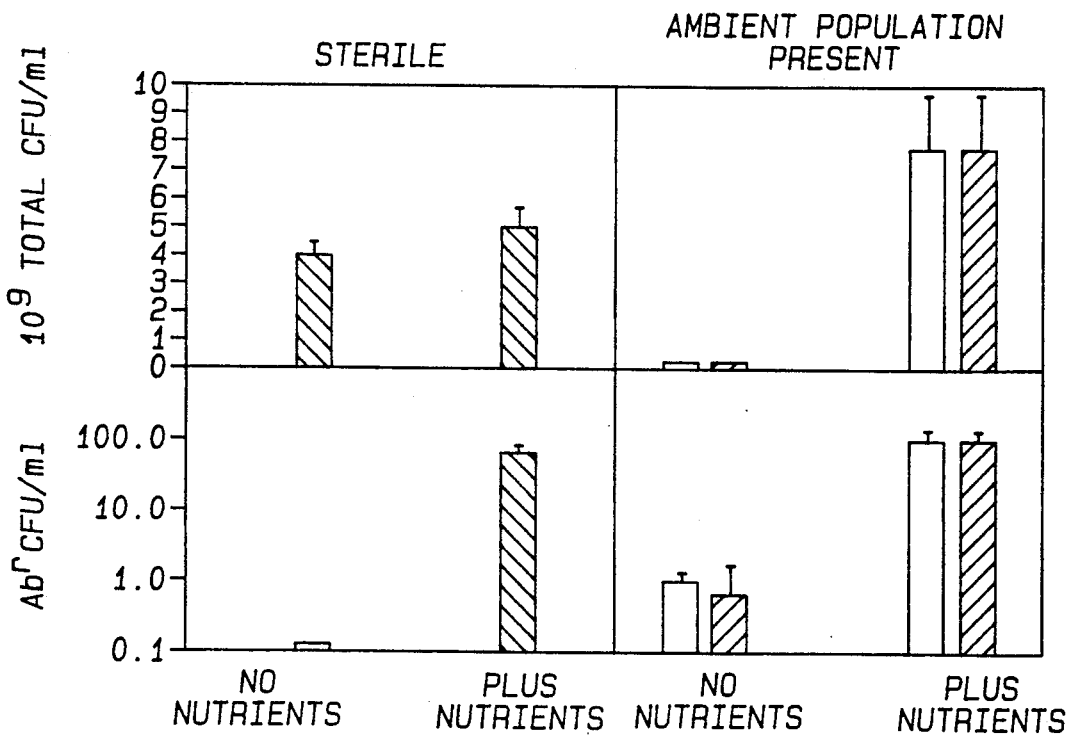
Figure 5C:
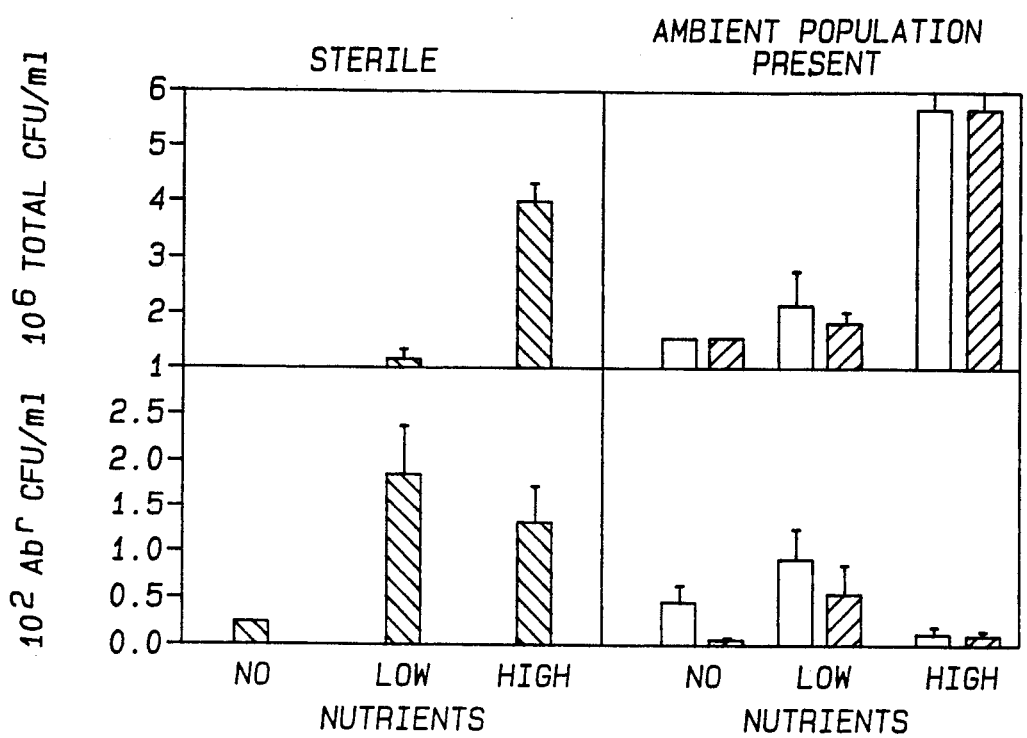

Water column microcosms: effect of nutrients. Addition of nutrients (P and Y) to water column microcosms stimulated growth of both the ambient population and the WJT-1C recipients in all treatments (FIG. 5). Total number of CFU (enumerated on nonselective media) was proportional to the amounts of P and Y added, as can be seen for the Bahamas surface-water experiment (FIG. 5C). The addition of nutrients also resulted in greater numbers of transformants in every experiments (FIG. 5). The least effect of nutrient addition was observed for the eutrophic estuarine environment, where the total number of transformants in the nutrient-amended sample was only twice that of the unamended sample. The ambient levels of dissolved nutrients in the estuarine sample probably allowed transformation as efficiently as in the nutrient-amended samples.

In four of six experiments, an increase in transformation frequency in nutrient-amended samples was observed (Table 5).

TABLE 5

Antibiotic resistance and transformation frequencies in water column microcosm experiments

| Environment[a] | Resistance[b] frequency | Transformation[c] frequency | Transformants[d]/Ab$^2$ cells (%) |
|---|---|---|---|
| Estuarine | | | |
| ASF | $1.33 \times 10^{-7}$ | $1.33 \times 10^{-7}$ | 100 |
| ASF + nut. | $8 \times 10^{-8}$ | $8 \times 10^{-8}$ | 100 |
| Raw | $1.2 \times 10^{-6}$ | $4.5 \times 10^{-9}$ | 0.3 |
| Raw − nut. | $6.8 \times 10^{-7}$ | $1.1 \times 10^{-7}$ | 11.1 |
| Oligotrophic Gulf of Mexico | | | |
| ASF | 0 | 0 | |
| ASF + nut. | $1.5 \times 10^{-6}$ | $1.5 \times 10^{-6}$ | 100 |
| Raw | $1.2 \times 10^{-6}$ | $1.2 \times 10^{-6}$ | 73 |
| Raw − nut. | $1.4 \times 10^{-6}$ | $1.4 \times 10^{-6}$ | 100 |
| Oligotrophic Bahamas | | | |
| ASF | $8 \times 10^{-7}$ | $8 \times 10^{-7}$ | 100 |
| ASF + low nut. | $1.7 \times 10^{-6}$ | $1.7 \times 10^{-6}$ | 100 |
| ASF + high nut. | $3.1 \times 10^{-7}$ | $3.1 \times 10^{-7}$ | 100 |
| Raw | $6.3 \times 10^{-7}$ | $7.6 \times 10^{-8}$ | 11.9 |
| Raw − low nut. | $5.8 \times 10^{-7}$ | $4.7 \times 10^{-7}$ | 60.2 |
| Raw − high nut. | $1.0 \times 10^{-8}$ | $1.5 \times 10^{-8}$ | 91.2 |

[a]ASF, autoclaved and sterile filtered; nut., sample amended with P and Y (see Materials and Methods); raw, nonsterile sediment with ambient community present.
[b]Frequency of appearance of resistant bacteria (total antibiotic-resistant CFU/total CFU).
[c]Number of WJT-1C transformants divided by total WJT-1C present.
[d]Number of WJT-1C transformants divided by total antibiotic-resistant (Ab$^2$)CPU × 100.

Low levels of nutrients (100 $\mu$g of P per ml, 20 $\mu$g of Y per ml) stimulated transformation in the presence or absence of the ambient community in Bahamian samples, whereas high levels of nutrients resulted in transfer frequencies below those found in the unamended samples. Thus, low levels of nutrients apparently stimulated transformation better than high levels of nutrients.

Water column transformation experiments: effect of the ambient population. The presence of the ambient population inhibited gene transfer in two of three experiments (estuarine and Bahamas water experiments: FIG. 5 and Table 5). The ambient population had no effect on transfer in the oligotrophic waters of the Gulf of Mexico (Table 5). This may have been caused by the numerical excess of the recipient compared with the ambient population in these waters. In all other experiments, the presence of ambient community resulted in approximately a one-log decrease in transformation frequency (Table 5), with the exception in the nutrient amended estuarine treatment.

Figure 6A:
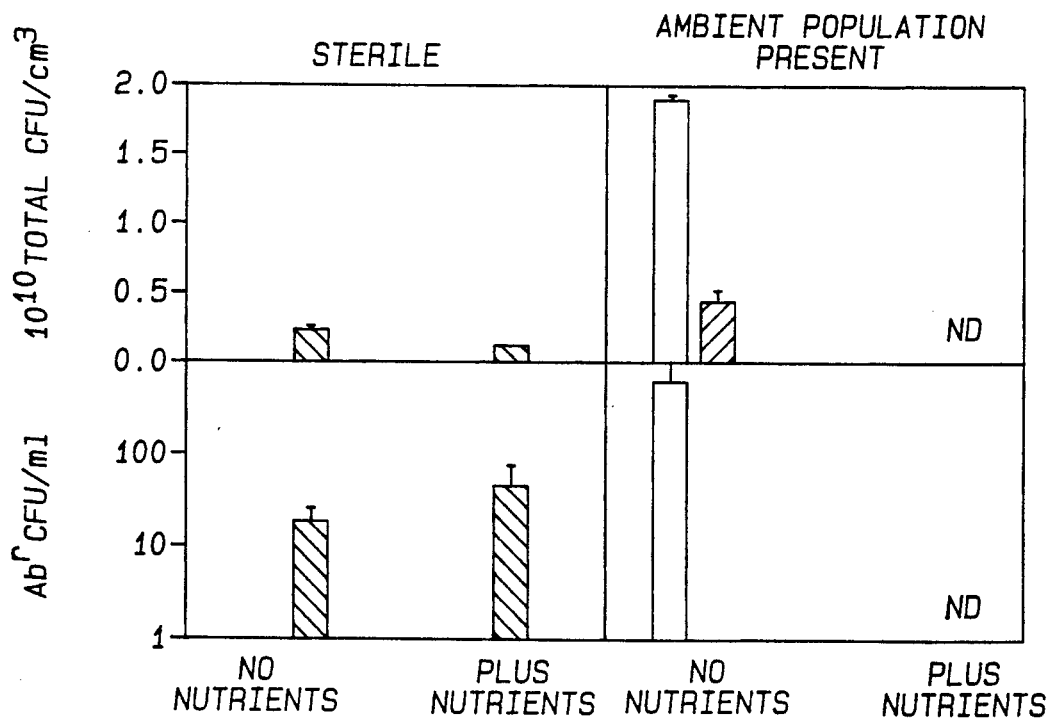
Figure 6B:
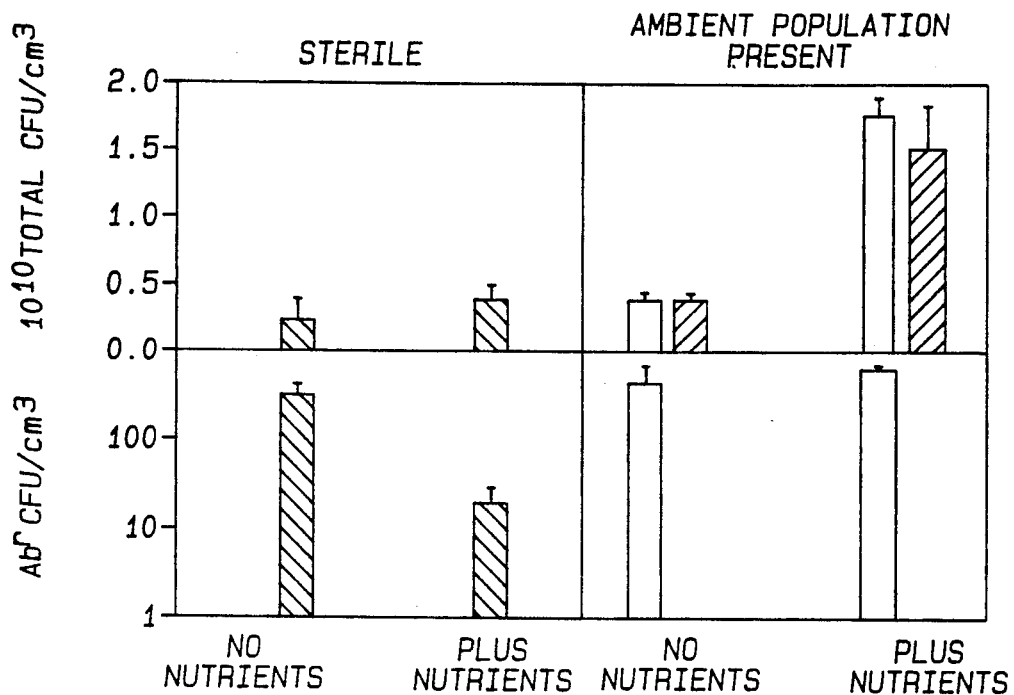
Figure 6C:
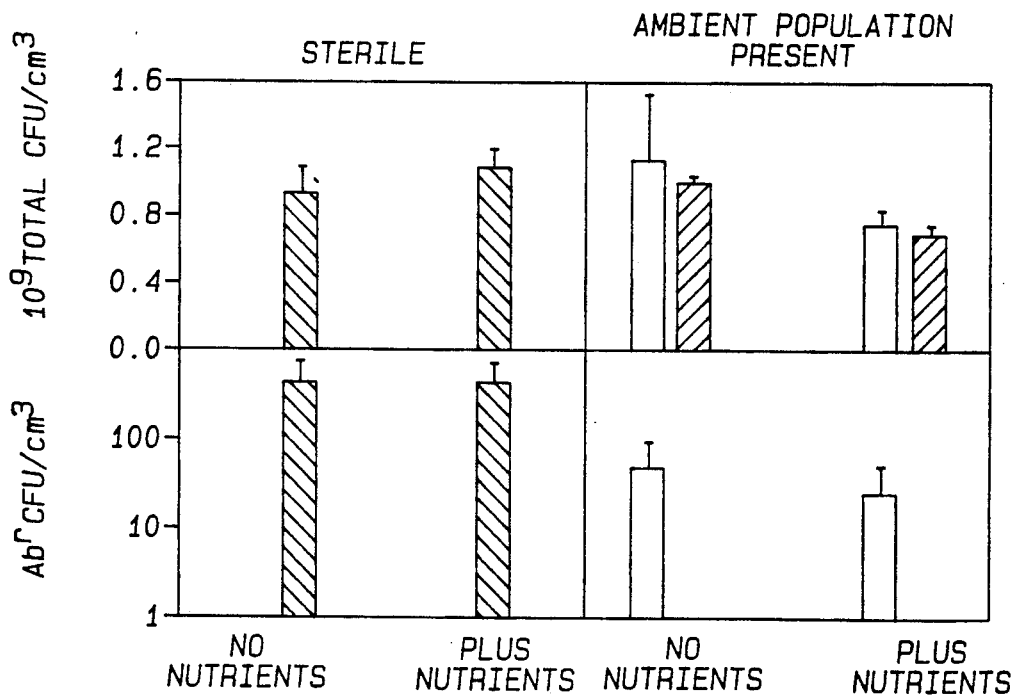

Sediment microcosm experiments. Transformation occurred in sterile-sediment microcosms at frequencies which were not significantly different than those observed in the water column (Table 6 and FIG. 6).

TABLE 6

Transformation in sediments and water column-sediment microcosms

| Environment[a] | Resistance[b] frequency | Transformation[c] frequency | Transformants[d]/ Ab² cells (%) |
|---|---|---|---|
| Estuarine | | | |
| Sterile sediment | 0 | 0 | |
| Sterile sediment + nut. | $1.5 \times 10^{-8}$ | $1.5 \times 10^{-8}$ | 100 |
| Raw sediment | $3.3 \times 10^{-8}$ | 0 | 0 |
| Gulf of Mexico Shelf | | | |
| Sterile | $6.6 \times 10^{-8}$ | $6.6 \times 10^{-8}$ | 100 |
| Sterile + nut. | $4 \times 10^{-9}$ | $4 \times 10^{-9}$ | 100 |
| Raw | $7 \times 10^{-8}$ | 0 | 0 |
| Raw + nut. | $1.75 \times 10^{-8}$ | 0 | 0 |
| Miami sediments | | | |
| Sterile | $5 \times 10^{-8}$ | $5 \times 10^{-8}$ | 100 |
| Sterile + nut. | $4.8 \times 10^{-8}$ | $4.8 \times 10^{-8}$ | 100 |
| Raw | $4.8 \times 10^{-9}$ | 0 | 0 |
| Raw + nut. | $3.5 \times 10^{-9}$ | 0 | 0 |
| oulter's Cay, Bahamas | | | |
| Sterile water column | $1.3 \times 10^{-8}$ | $1.3 \times 10^{-8}$ | 100 |
| Sterile water column + sediments | $1.2 \times 10^{-8}$ | $1.2 \times 10^{-8}$ | 100 |
| Sterile sediments | $1.8 \times 10^{-7}$ | $1.8 \times 10^{-7}$ | 100 |
| Raw water column | $3.8 \times 10^{-9}$ | $2.7 \times 10^{-10}$ | 6.7 |
| Raw water column + sediments | $6.6 \times 10^{-7}$ | 0 | 0 |
| Raw sediments | $4.4 \times 10^{-7}$ | 0 | 0 |

[a]nut., sample amended with P and Y (see Materials and Methods); raw, nonsterile sediment with ambient community present.
[b]Frequency of appearance of resistant bacteria (total antibiotic-resistant FU/total CFU).
[c]Number of WJC-1C transformants divided by total WJC-1C present.
[d]Number of WJC-1C transformants divided by total antibiotic-resistant Ab²) CFU × 100.

The addition of nutrients had no consistent effect on transformation and stimulated transfer in only one of three experiments (estuarine samples). These results imply that transformation was not nutrient limited in the sediments investigated. The greatest effect on transformation was observed in nonsterile sediments. No transformation in the presence of the ambient community in any sediment environment was observed.

Figure 7:
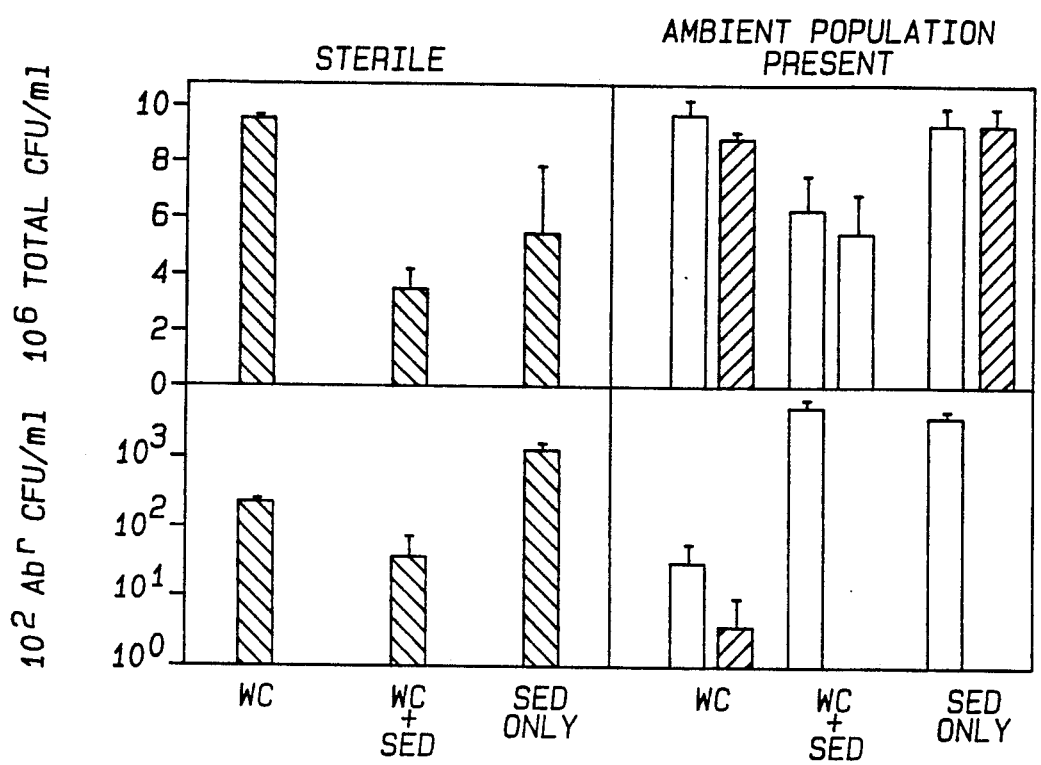

Sediment-water column microcosm experiments. To determine the effect of the presence of sediments on gene transfer in the water column, experiments on liquid transformation in the presence of sediments were performed, and results were compared with those for experiments with liquid only and sediment only (FIG. 7 and Table 6). In sterile microcosms, transformation in water column, water plus sediment, and sediment environments was detected, with greatest frequency in the sediment ($1.8 \times 10^{-9}$ compared with $1.2 \times 10^{-8}$ to $1.3 \times 10^{-8}$; Table 6). When the ambient population was present, transfer was observed only in the water column statement. The presence of nonsterile sediment inhibited the transformation process, even in the water column-plus-sediment treatment (FIG. 7 and Table 1). The number of antibiotic resistant bacteria in the sediments exceeded that of the water column by nearly two orders of magnitude. It may be that the sediment bacteria outcompeted the transformants for nutrients and-/or transforming DNA. In no experiment was transfer to the ambient population observed.

The above experiments demonstrate the capability for natural plasmid transformation to occur in marine water column environments in the presence or absence of the ambient microbial community. The frequencies of transfer observed ranged from $1.7 \times 10^{-6}$ to $2.7 \times 10^{-10}$ transformants per recipient and were generally several orders of magnitude below that observed for filter transformation assays ($10^{-6}$ to $2.5 \times 10^{-4}$). Therefore, transformation in water column environments seems more likely to occur when cells are used as DNA donors than with free DNA.

The ecological significance of the findings with nutrients is that transformation is probably more likely to occur in environments receiving organic inputs than in oligotrophic environments. Thus estuaries, waters receiving sewage or other nutrient-rich effluents, wastewater treatment facilities and other environments with organic carbon inputs favor transfer by transformation (and probably gene transfer by other mechanisms). In oceanic water column environments, transformation may occur in microenvironments associated with detrital particles, in marine snow, in Trichodesmium colonies, in Sagassum communities, during transient events such as photoplankton blooms, or during upwelling events.

The significance of this data is an efficient transformation system with identifiable markers for use in freshwater or marine water column and sediment (and potentially soil) environments. Using this system, it shows the first instance of natural plasmid transformation in seawater and in the presence of the ambient community in seawater. Our results indicate that there is a greater likelihood of transformation occurring in the water column than in marine sediments.

EXPERIMENTAL EVIDENCE #3

The following experiments demonstrate the cell-contact dependent transfer of plasmid DNA from a laboratory E. coli strain to a marine Vibrio species. This data is the first demonstration of intergeneric natural plasmid transformation involving a marine bacteria. The data below shows that the process was transformation on the basis that it was completely inhibited by DNase I. Neither strain contained conjugative elements or phages.

From the data below, it can be concluded that the transforming DNA was apparently located on the donor cell surface because no transfer occurred by spent media or when donor and recipient were separated by filters. Equally important is the fact that dead cells served equally well as donors as viable cells and transfer was demonstrated in sterile and nonsterile marine microcosms.

These results are pertinent with regard to the permitting process for use of genetically modified organisms in the environment pursuant to the method of the present invention, as well as the treatment of waste water, in that nonviable cells entering into a aquatic environments may continue to serve as reservoirs of transforming DNA. Accordingly, the present invention provides an assay for determining the predisposition of such microorganisms, living or dead, or genetic material, to cause genetic pollution, as previously described. Secondly, cell contact dependent transformation may be a mechanism for the intergeneric disseminate nonconjugative plasmids between bacteria in aquatic environments. Such processes can have significant effects on the genetic structure of aquatic microbial communities.

Materials and Methods

Natural plasmid transformation of Vibrio JT-1. E. Coli RM1259 (MV10-K12 C600 a trp Et F.), containing plasmid pQSR50, a 14.3 kb nonconjugative plasmid (16), was used as plasmid donor as indicated. The recipient (Vibrio JT-1) was a nalidixic acid, rifampicin resistant derivative of the High frequency of Transformation (HfT) strain Vibrio WJT-1C (29). E. coli donor cells were grown overnight at 37° C. in Luria-Bertani broth containing 50 μg/ml streptomycin. Vibrio JT-1 cells were grown overnight at 28° C. in ASWJP containing 150 μg/ml rifampicin and 500 μg/ml nalidixic acid. Transformation assays were performed either by cofiltering 1 ml of donor and recipient (filter assays; transformation frequency $[F_R]$—$10^{-7}$) or by mixing one ml each of donor and recipient cell suspension (liquid or broth matings; $F_R$—$10^{-6}$). In either instance, cells were washed twice in media, prior to assay, to remove any residual extracellular DNA if such had been extruded into the media during growth.

The plasmid DNA employed was the nonconjugative plasmid pQSR50 (16), a derivative of R1162 containing Tn5. Assays were performed using Sterile 0.2 μm Nuclepore filters (25 mm diameter) and liquid assays were performed in a final volume of 2.0 ml. For DNase treatment, 200 Kunitz units of DNAse was added to the filter surface (filter transformation assays) or to liquid mating mixtures. All transformation incubations were performed for 18–24 hours, followed by plating on respective growth media to enumerate donors and recipients, and ASWJP containing 500 μg/ml kanamycin, 100 μg/ml streptomycin, 150 μg/ml rifampicin, and 500 μg/ml nalidixic acid to detect transformants. For matings performed in the presence of nalidixic acid and rifampicin, these inhibitors were added to two ml incubation mixtures for a final concentration of 500 and 150 μg/ml, respectively. For heat inactivation of donor cells, cells were heated in 1.0 ml aliquots for 20 and 3 minutes at 70° C., a process which resulted in no viable donor cell. For separation of donor and recipient cells by a 0.2 μm filter in a filter assay, one ml each of donor and recipient were filtered onto separate 0.2 μm Nuclepore filters, and the filters placed one on top of the other (cell spot not touching) on an ASWJP agar plate and incubated overnight. For separation of donor and recipients in liquid, the respective cultures were added to separate sides of a Spectrum separation cell, with a 0.2 μm Nucleport filter dividing the donor and recipient cells. For transformation with plasmid monomers, large scale purification of pQSR50 was performed as previously described (29).

Plasmid transfer from E. coli to Vibrio JT-1 by natural plasmid transformation in marine microcosms For transfer in sterile artificial seawater, washed cell suspension of donor (E. coli RM1259) and recipient (Vibrio JT-1) were resuspended in ASWJP media lacking any organic nutrients (30). Cells were incubated at 28° C. For autoclaved, sterile filtered estuarine microcosms, Bayboro Harbor, St. Petersburg, Fla. water was autoclaved and sterile filtered through a 0.2 μm Nuclepore filter, and transformation assays performed as for artificial seawater. Sterile filtered and nonsterile estuarine microcosms used freshly collected Bayboro Harbor water that was 0.2 μm filtered or unfiltered, respectively. At the end of the incubation period (about 20–24 hours), the cells were harvested directly (4ml microcosms) or by 0.2 μm filtration (all other volumes). The filters were resuspended in 5.0 ml ASWJP and plated on the appropriate media as described. For sterile sediment microcosms 3 cc of sterile sediment taken from Joulter's Cay, Bahamas, was inoculated with donor and recipient cell suspension s (0.1 ml), the sediment mixed and overlaid with 1.5 ml ASWJP media. Sediments were incubated overnight, and 3.5 ml ASWJP added. The sediments were vortexed vigorously, allowed to settle, and the supernatant plated on media as described above.

Filter assays. For filter assays with purified plasmid, multimers were made in vitro as previously described (29). Vibrio recipients were filtered and DNase I added at the appropriate times. After 24 hours, the filters were resuspended in 10.0 ml ASWJP and aliquots plated on ASWJP media (total Vibrio counts) or ASWJP containing 500 μg/ml kanamycin and 1000 μg/ml streptomycin (to enumerate transformants). For filter assays with donor cells, one ml each of donor and recipient culture was filtered, placed on an ASWJP plate for the prerequisite length of time, and cells plated as described above. For liquid assays, the incubations were terminated by addition of DNase, and plated as described above. When incubations were terminated without DNase (for example, after 10 minutes of coincubation of donor and recipient), no transfer was detected, indicating that transfer did not occur on the plates used to enumerate transformants.

RESULTS

The above data demonstrates that all transfer was DNase sensitive. By definition (5), this process was transformation. No transfer occurred in the absence of the donor or transforming DNA and there was no rate of spontaneous mutation of the Vibrio to kanamycin and streptomycin resistance, the markers encoded by the transforming plasmid DNA.

The transformed Vibrio cells were verified for plasmid acquisition by molecular probing by colony hybridization with a probe made from the transforming plasmid DNA (29).

As shown in Table 7, when donor and recipient cells were filtered on separate filters and the filters placed one on top of the other so as to separate cell spots, no transfer occurred. On the other hand, if the cell spots touched each other, then transfer did occur, as demonstrated by the dated set forth in Table 7.

TABLE 7

Natural Plasmid Transformation of Vibrio JT-1.

| Treatment of Conditions | Form of Transforming DNA | Filter (F) or Liquid (L) Nating | Transformation Frequency | |
|---|---|---|---|---|
| | | | Per Donor ($F_D$) | Per Recipient ($F_R$) |
| E. coli + Vibrio | Whole viable cells | L | $1.4 \pm 0.7 \times 10^{-6}$ | $2 \pm 0.7 \times 10^{-6}$ |
| E. coli + Vibrio | Whole viable cells | F | $1.7 \pm 1.5 \times 10^{-6}$ | $5.2 \pm 3.7 \times 10^{-7}$ |
| Vibrio only | none | F,L | 0 | 0 |
| E. coli + Vibrio + DNase | Whole viable cells | F,L | 0 | 0 |
| E. coli + Vibrio | Heat killed donor cells | L | — | $2.7 \pm 2.5 \times 10^{-6}$ |
| E. coli + Vibrio | Heat killed donor cells | F | — | $2.67 \pm 3.2 \times 10^{-7}$ |
| E. coli + Vibrio in Nal/RH media | Donor cells impaired | L | $2.9 \times 10^{-8}$ | $1.9 \times 10^{-8}$ |
| E. coli + Vibrio in Nal/rif media | Heat killed donors | L | | $8.2 \times 10^{-7}$ |

TABLE 7-continued

Natural Plasmid Transformation of Vibrio JT-1.

| Treatment of Conditions | Form of Transforming DNA | Filter (F) or Liquid (L) Mating | Transformation Frequency | |
|---|---|---|---|---|
| | | | Per Donor ($F_D$) | Per Recipient ($F_R$) |
| E. coli + Vibrio separated by 0.2 μm filter | Whole viable cells | F,L | 0 | 0 |
| E. coli + Vibrio separated by 0.2 μm filter | Heat killed donor cells | L | 0 | 0 |
| Vibrio only | 4 μg purified plasmid monomers | L | — | $9.0 \pm 0.7 \times 10^{-7}$ |
| Vibrio only | plasmid DNA extract, 1.0 ml culture | L | — | 0 |
| Vibrio only | plasmid DNA extract, 5.0 ml culture | L | — | $6.3 \times 10^{-10}$ |
| Vibrio only in Nal/rif media | 4 μg purified plasmid monomers | L | — | $4.2 \times 10^{-7}$ |

Similarly, 10 ml donor and recipient cell suspensions separated by 0.2 μm filter in a dialysis chamber resulted in no transfer. Additionally, the plasmids apparently did not leak freely from the donor cells, because no transfer occurred from spent media as further shown in Table 7. Therefore, the above data demonstrates that there was a requirement for contact between the E. coli and Vibrio cells for transfer to occur. Hence, the cell line of the present invention ca be used in an assay with host cell microorganisms to test for the propensity of such cells to transform by the method of cell-contact dependent transfer of plasmid DNA.

The presence of the donor cells facilitated gene transfer. Transfer is documented in the presence of high concentrations of highly purified plasmid DNA (i.e. 4 μg; $F_R = \sim 10^{-5}$ for filter and $10^{-7}$ for liquid assays; Table 7). When the plasmid DNA was purified from one ml of donor culture by either foiling lysis or alkaline lysis miniprep procedure (19), no transfer occurred. Plasmid DNA prepared from one of two 5 ml cultures yielded one transformant colony, resulting in a frequency of transformation 2700 fold lower than if 1 ml of whole donor cells ($3-5 \times 10^9$ cells) was used as transforming DNA. Estimations of plasmid DNA content of E. coli donors from 1) large scale plasmid preparations, 2) calculation based on an assumption of a cop number of 10 (common for RSF1010/R1162-type derivatives; Greg Steward, personal communication), or 3) agarose gel electrophoresis, Southern Transfer, and molecular probing of donor cell minipreps suggests that 1.0 ml culture would yield 0.25-0.5 μg plasmid. This amount of DNA would result in perhaps barely detectable levels of transfer in liquid matings. It seems unlikely that all plasmid in intact E. coli cells would be accessible to recipient cells (i.e. on the cell surface). It may be that the plasmid on the donor cells surface is in a highly transformable form, more so than that purified from cells by conventional plasmid purification methods (perhaps in oligomers, etc.). Or, the plasmid may be membrane bound and in a form more likely to penetrate the recipient cell's membrane-wall complex.

When DNA synthesis of the donor cells was inhibited by nalidixic acid, transfer was reduced by nearly two orders of magnitude, indicating a requirement for DNA synthesis for extrusion of DNA onto the cell surface. Cells that had been killed by heating also transformed as well as viable cells, perhaps owing to conformational changes in the cell surface that facilitated plasmid transport to the extracellular environment Heating did not result in cell lysis, as determined by epifluorescence microscopy, and heated cell suspensions did not release filterable transforming DNA. Thus, dead cells could participate in cell contact-dependent transformation in the environment.

Figure 8:
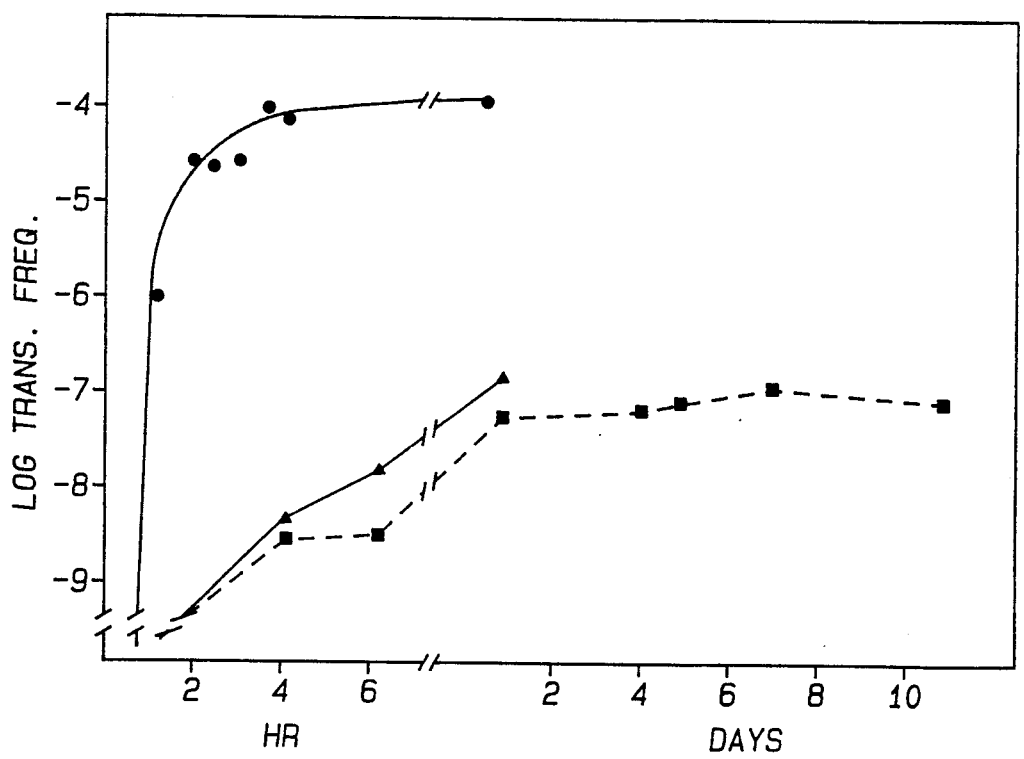

The kinetics of transfer by cell contact-mediated transfer indicate that the process was slower than that observed with highly purified plasmid in filter matings (FIG. 8). For example, transformation with highly purified plasmid DNA was detectable within one hour of addition of plasmid and reached maximal frequency at four hours. When intact donor cells were used as a source of transforming DNA, maximal frequency was found at 24 hours. This is consistent with the synthesis and extrusion of plasmid on the cell surface over the mating period.

The above data demonstrates the ability of the present invention to provide a high frequency of transformation strain of an estuarine Vibrio species. The above data further demonstrates the ability of the present invention to be used and method of detecting the propensity of plasmid transformation in an aqueous or sediment environment. The data demonstrates the ability of the present invention to be used to determine if a type of DNA is capable of transformation (i.e. using purified DNA, semipure preparations, or cell lysates). The invention also can enable determination if strains can serve as donors for transformation. Such strains should not be used in the environment, because of the potential to genetically modify indigenous bacteria by transfer of their recombinant DNA for such flora.

The invention has been described in an illustrative manner, and it is to be understood that the terminology which has been used is intended to be in the nature of words of description rather than of limitation.

Obviously many modifications and variations of the present invention are possible in light of the above teachings. It is, therefore, to be understood that within the scope of the appended claims, the invention may be practiced otherwise than as specifically described.

What is claimed is:

1. A substantially pure form of high frequency of transformation strain of an estuarine Vibrio species selected from the group consisting of WJT-1C, MF-4C, and JT-1, said strain being derived from a parent strain naturally transformable with broad-host-range plasmids, said strain having a crenate colony morphology being rod shaped motile with single polar flagellum, oxidase positive and able to ferment glucose, said strain being generated from the parental Vibrio strain, transformed by broad-host-range plasmid multimers, and cured of said plasmid by growth of plasmid transformants in nonselective medium resulting in said cured high frequency of transformation strain that transform significantly more frequently than the parental strain.

2. A transformation strain as set forth in claim 1 wherein said plasmids are Inc P4 and MC P1 plasmids.

3. A transformation strain as set forth in claim 2 wherein said plasmids are selected from the group consisting of pGQ3, pQSR50, pKT230, R1162, pLV1013, and pAM120.

4. A transformation strain as set forth in claim 1 wherein said parent Vibrio strain is Vibrio sp. strain DI-9.

5. A transformation strain as set forth in claim 1 wherein said parent Vibrio strain is *V. parahaemolyticus*.

* * * * *